United States Patent

Dapperheld et al.

Patent Number: 5,374,737
Date of Patent: Dec. 20, 1994

[54] PROCESS FOR THE PREPARATION OF 2-AMINOBENZOTHIAZOLES

[75] Inventors: Steffen Dapperheld, Hofheim am Taunus; Heinrich Volk, Bad Vilbel; Karl Peter, Rodenbach, all of Germany

[73] Assignee: Hoechst Aktiengesellschaft, Frankfurt am Main, Germany

[21] Appl. No.: 153,782

[22] Filed: Nov. 16, 1993

Related U.S. Application Data

[63] Continuation of Ser. No. 938,298, Aug. 28, 1992, abandoned.

[30] Foreign Application Priority Data

Aug. 30, 1991 [DE] Germany ............... 4128872

[51] Int. Cl.⁵ .................................... C07D 277/82
[52] U.S. Cl. .......................................... 548/164
[58] Field of Search ................................. 548/164

[56] References Cited

U.S. PATENT DOCUMENTS 4,363,913 12/1982 Clark et al. ............... 548/164
4,719,304 1/1988 Rentil et al. ............... 548/164

FOREIGN PATENT DOCUMENTS 0207416 7/1987 European Pat. Off. .
57-9774 1/1982 Japan .
0167576 10/1983 Japan .

OTHER PUBLICATIONS

Chemical Abstracts, vol. 96, No. 25, 1982; abstract No. 217832q, p. 744; Zusammenfassung & JP-A-82 009 774 (Nippon Kayaku Co Ltd) Jan. 19, 1982.

Primary Examiner—Joseph Paul Brust
Assistant Examiner—MarySusan H. Gabilan

[57] ABSTRACT

A process for the preparation of a 2-aminobenzothiazol of the formula (I)

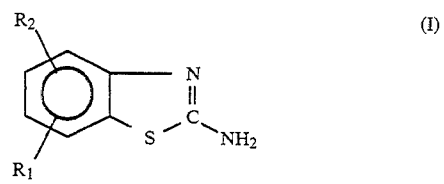

in which $R_1$ and $R_2$ independently of each other are hydrogen, fluorine, chlorine, bromine or iodine, trifluoromethyl or $C_1$-$C_4$-alkyl, $C_1$-$C_4$-alkoxy or nitro groups, by conversion of an arylthiourea of the formula (II)

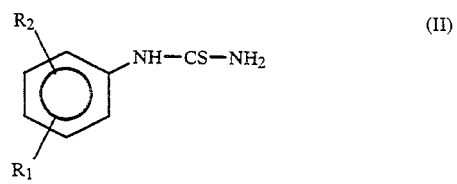

in which $R_1$ and $R_2$ have the meaning mentioned, which comprises carrying out the conversion in 99 to 100% strength of sulfuric acid with continuous addition of catalytic amounts of bromine, hydrogen bromide or bromide in the form of aqueous solutions and using an arylthiourea of the formula (II) which contains 1 to 35% water.

19 Claims, No Drawings

PROCESS FOR THE PREPARATION OF 2-AMINOBENZOTHIAZOLES

This case is a continuation of U.S. Ser. No. 07/938,298, filed Aug. 28, 1992, now abandoned.

2-Aminobenzothiazoles are important intermediates for the preparation of pigments and crop protection agents.

It is known to prepare 2-aminobenzothiazoles by cyclisation of the corresponding arylthioureas in at least 85% strength sulfuric acid in the presence of catalytic quantities of bromine, hydrogen bromide, sodium bromide, potassium bromide or ammonium bromide at temperatures of from 2° to 120° C. (Japanese Patent Application Sho 57-9774; U.S. Pat. No. 4,363,913). However, the reaction does not proceed uniformly so that qualitatively unsatisfactory product mixtures result from side reactions (sulfation, bromination, hydrolysis of the phenylthiourea with, in part, subsequent substitutions of the first-mentioned type), which mixtures require a laborious purification and (in the case of small solubility differences between the target products and by-products) give poor yields.

However, these processes suffer from the disadvantage that the arylthioureas used are only used in the dry state. In addition, the yields are mostly unsatisfactory.

Drying of these compounds in this case is a process which is industrially problem-free, but which negatively influences the economic efficiency of the process, since the mostly highly toxic and very dusty products should only be handled in practice in compliance with expensive safety measures.

By means of the present invention, a process for the preparation of 2-aminobenzothiazoles is now made available in which the disadvantages mentioned of the conventional processes no longer occur.

It has now been found that 2-aminobenzothiazoles of the formula (I) (see Patent claim 1), in which $R_1$ and $R_2$ independently of each other are hydrogen, fluorine, chlorine, bromine or iodine, trifluoromethyl or $C_1$-$C_4$-alkyl, $C_1$-$C_4$-alkoxy or nitro groups, can be prepared in high yield and purity by conversion of arylthioureas of the formula (II) (see Patent claim 1), in which $R_1$ and $R_2$ have the same meaning, if the conversion is carried out in 99 to 100% strength sulfuric acid with continuous addition of catalytic quantities of bromine, hydrogen bromide or bromide in the form of aqueous solutions and if arylthioureas of the formula (II) are used which contain 1 to 35% water.

Bromides which can be used are for example alkali metal bromides, ammonium bromide and tetraalkylammonium bromide, but preferably sodium bromide, potassium bromide or ammonium bromide.

Preferred compounds of the formula (I) are: 4-chloro-, 6-chloro-, 5,6-dichloro-, 4-fluoro-, 6-fluoro-, 6-nitro-, 4-nitro-, 6-methoxy-, 6-ethoxy-, 6-methyl-, 6-ethyl-, 4-trifluoromethyl-, 6-trifluoromethyl-2-aminobenzothiazole.

Of the compounds of the formula (II), 2-chloro-, 4-chloro-, 3,4-dichloro-, 2-fluoro-, 4-fluoro-, 4-trifluoromethyl-, 2-nitro-, 4-nitro-, 4-methoxy-, 4-ethoxy-, 4-methyl-, 2-methyl-, 2-ethyl-, 4-ethylphenylthiourea are particularly preferred. These compounds preferably contain 2 to 25%, in particular 3 to 20%, water.

The starting compounds (II) may be prepared by conventional methods, such as for example as described in Houben-Weyl, Methoden der Organischen Chemie, [Methods in Organic Chemistry] Vol. 9 (1955), p. 888.

The compounds of the formula (II) are dissolved in 99 to 100% strength sulfuric acid, preferably in 100% strength sulfuric acid. The amount of sulfuric acid is generally at least 1.5 times the amount of arylthiourea used, preference is given to the use of 1.9 to 5-fold, in particular to 2 to 3.4-fold amounts of sulfuric acid. The use of larger amounts of sulfuric acid is possible, but reduces the economic efficiency of the process.

Relative to the total amount of arylthiourea and sulfuric acid used, a water content generally of 2 to 20% by weight, preferably of 2.5 to 15% by weight, in particular of 3 to 8% by weight is an advantage.

The process according to the invention is generally carried out at temperatures between 10° and 130° C. preferably between 20° and 100° C. The reaction temperature essentially depends on the type of the substituents $R_1$ and $R_2$, since the use of compounds having electronegative substituents generally requires higher temperatures than the use of compounds having electropositive substituents.

The bromide, which is added in catalytic amounts to the reaction solution, can be continuously metered in as the solid or in the form of an aqueous solution, as an aqueous solution of hydrogen bromide or as elementary bromine. Preference is given to the continuous addition of aqueous solutions of ammonium bromide, sodium bromide or potassium bromide, or hydrogen bromide, in particular the continuous addition of ammonium bromide solution. The aqueous solutions of these substances are used as concentrated as possible, in order to reduce the content of the 99 to 100% strength sulfuric acid used as little as possible. Preference is given to the use of saturated solutions. The amount of bromide used is generally between 0.01 and 10 mol %, preferably between 0.1 and 5 mol %, relative to the amount of arylthiourea used.

The waste gas ($SO_2$) produced is converted in a gas scrubber operated with alkali metal hydroxide solution to give reusable bisulfite solution.

The progress of the reaction is easily followed by analytical methods, such as thin layer chromatography, gas chromatography or liquid chromatography.

After complete conversion of the starting compounds, the reaction mixture is diluted with water and the 3-aminobenzothiazole formed of the formula (I) is precipitated out in the form of its sulfate by cooling or is precipitated as the free base by addition of alkali metal hydroxide solution or aqueous ammonia solution and is isolated by filtration.

EXAMPLES 1. 117.6 g of 2-chlorophenylthiourea having a dry matter content of 85% were dissolved at 20° to 25° C. in the course of half an hour in 324 g of $H_2SO_4$ (100%). The weight ratio of sulfuric acid to 2-chlorophenylthiourea (100%) was 3.24 and the water content, relative to the sum of 2-chlorophenylthiourea and $H_2SO_4$, was 3.98% by weight. The mixture was then heated to 70° C., and in the course of 4 hours, 12 ml of a 40% strength $NH_4Br$ solution was added dropwise. The resulting solution was stirred into 400 ml of water and was stirred for one hour at 70° C. The mixture was cooled to 20° C. and filtered off by suction. The filter residue was placed in a solution of 1150 ml of water and 50 g of NaOH and was stirred for one hour at 70° C. The mixture was then filtered off using suction and the residue was washed free of sulfate with water and dried.

Yield: 94.3 g of 4-chloro-2-aminobenzothiazole (96.7%), melting point: 202°–203° C.

2.–5. The procedure of Example 1 was carried out, but the 2-chlorophenylthiourea was replaced by the compounds listed in Table 1.

stirred into 400 ml of water and was stirred for one hour at 70° C. It was cooled to 20° C. and filtered using suction. The filter residue was placed in a solution of 1,150 ml of water and 50 g of NaOH and was stirred for one hour at 70° C. The mixture was then filtered using suction and the filtration residue was washed free of sulfate with water.

TABLE 1

| Example | Arylthiourea (II) | Dry matter content in % | Weight ratio sulfuric acid to arylthiourea | Water content in % by weight* | Product | Yield in % (m.p.) |
| --- | --- | --- | --- | --- | --- | --- |
| 2 | 4-chlorophenyl-thiourea | 86 | 2.82 | 4.10 | 2-amino-6-chloro-benzothiazole | 95.1 (185–187) |
| 3 | 4-fluorophenyl-thiourea | 82 | 2.41 | 6.07 | 2-amino-6-fluoro-benzothiazole | 94.3 (181) |
| 4 | 3,4-dichlorophenyl-thiourea | 90 | 2.05 | 3.51 | 2-amino-5(7),6-dichlorobenzothiazole (mixture of isomers) | 96.2 |
| 5 | 2-chlorophenyl-thiourea | 80 | 3.24 | 5.56 | 2-amino-4-chloro-benzothiazole | 97.1 (202) |
| 6 | 4-nitrophenyl-thiourea | 89 | 3.45 | 2.71 | 2-amino-6-nitro-benzothiazole | 86.2 (245–246) |

*)relative to the sum of arylthiourea and sulfuric acid 7. 100 g (0.5 mol) of 4-methoxyphenylthiourea (dry matter content 91%) were dissolved in the course of half an hour at 20° to 25° C. in portions in 290 g of H₂SO₄ (100%). The weight ratio of sulfuric acid to 4-methoxyphenylthiourea (100%) was 3.19 and the water content was, relative to the sum of 4-methoxyphenylthiourea and sulfuric acid, 2.47% by weight. In the course of three hours, 30 g of a 40% strength NH₄Br solution were then continuously metered in at 25° to 30° C. The solution was then added to 1,200 g of water, clarified by filtration at 50° C. and adjusted to pH=8 with 430 ml of a 33% strength NaOH solution (143 g NaOH). The mixture was stirred for half an hour at 40° C. and filtered using suction. The residue was washed free of sulfate with 1,500 g of water and was then dried.

Yield: 85 g of 2-amino-6-methoxybenzothiazole (94.4%), melting point: 160°–161° C.

8. 108.3 g of 4-chlorophenylthiourea (dry matter content 86.1%) were dissolved at 20° C. in 320 g of H₂SO₄ (100%). The weight ratio of sulfuric acid to 4-chlorophenylthiourea was 3.4 and the water content, relative to the sum of 4-chlorophenylthiourea and sulfuric acid, was 3.51% by weight. In the course of 3 hours, 6 g of HBr solution (48% strength) were then added continuously. The temperature was maintained for 1.5 hours at 45° to 50° C. and then for 6 hours at 65° to 70° C. The solution was cooled to 20° C. and 250 ml of methanol were added. The temperature rose to approximately 70° C. The mixture was then cooled to 20° C. and filtered using suction. The filter residue was washed three times each time with 150 ml of acetone and dried in air.

Yield: 122.6 g of 2-amino-6-chlorobenzothiazole sulfate (87.7%).

COMPARISON EXAMPLES 1. 100 g (0.53 mol) of 2-chlorophenylthiourea (100%) were dissolved at 20° to 25° C. in the course of half an hour in 324 g of H₂SO₄ (95%). The weight ratio of sulfuric acid (100%) to 2-chlorophenylthiourea was 3.08 and the water content, relative to the sum of 2-chlorophenylthiourea and sulfuric acid, was 3.8% by weight. The mixture was then heated to 70° C. and 12 ml of a 40% strength NH₄Br solution were added in the course of 4 hours. The resulting solution was Yield: 79 g of 4-chloro-2-aminobenzothiazole (81%), melting point: 200°–201° C.

2. This example is a direct reworking of Example 6 from U.S. Pat. No. 4,363,913 and can be compared directly with Example 8 according to the invention. 93.3 g of 4-chlorophenylthiourea were dissolved at 20° C. in 150 ml of H₂SO₄ (98%). The weight ratio of sulfuric acid to 4-chlorophenylthiourea was 3.0 and the water content, relative to the sum of 4-chlorophenylthiourea and sulfuric acid, was 1.5% by weight. In the course of 3 hours, 1 g of HBr solution (48% strength) was then added each time at 30 minute intervals. The temperature was maintained for 1.5 hours at 45° to 50° C. and then for 6 hours at 65° to 70° C. The solution was cooled to 20° C. and 250 ml of methanol were added. The temperature rose to approximately 70° C. The mixture was then cooled to 20° C. and filtered using suction. The filter residue was washed three times, each time with 150 ml of acetone, and dried in air.

Yield: 99.7 g of 2-amino-4-chlorobenzothiazole sulfate (Repeat experiment: 10 1.4 g ), average yield: 100.55 g (71.9%).

3. The procedure of Comparison Example 2 was followed, but 108.3 g of 4-chlorophenylthiourea having a dry matter content of 86.1% were used. The weight ratio of sulfuric acid to 4-chlorophenylthiourea was 3.4 and the water content, relative to the sum of 4-chlorophenylthiourea and sulfuric acid, was 5.37% by weight.

Yield: 35.5 g of 2-amino-6-chlorobenzothiazole sulfate (25.4%).

We claim:

1. A process for the preparation of a 2-aminobenzothiazole of formula (I)

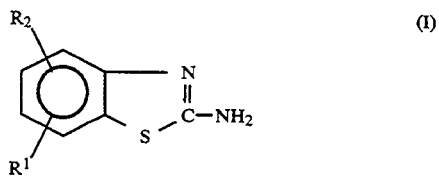

in which $R_1$ and $R_2$ independently of each other are hydrogen, fluorine, chlorine, bromine or iodine, trifluoromethyl or $C_1$-$C_4$-alkyl, $C_1$-$C_4$-alkoxy or nitro groups, comprising the following steps:

a. dissolving in 99 to 100% strength sulfuric acid a water-containing arylthiourea of formula (II)

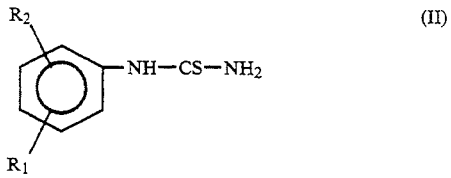

in which $R_1$ and $R_2$ are as defined in said formula (I), the amount of water in said arylthiourea being 1% to 35% by weight, and b. subsequently, in the resulting solution in sulfuric acid, catalyzing the cyclization of said arylthiourea with a catalytic amount of bromine or a bromide.

2. The process as claimed in claim 1, wherein said sulfuric acid is 100% strength sulfuric acid.

3. The process as claimed in claims 1 or 2, wherein said bromide is sodium, potassium, or ammonium bromide.

4. The process as claimed in claims 1 or 2, wherein said bromide is hydrogen bromide.

5. The process as claimed in claims 1 or 2, wherein said amount of water in said arylthiourea is 2 to 25% by weight.

6. The process as claimed in claims 1 or 2, wherein said amount of water in said arylthiourea is 3 to 20% by weight.

7. The process as claimed in claims 1 or 2, wherein said bromide is added continuously to said resulting solution.

8. The process as claimed in claims 1 or 2, wherein said bromide is continuously added to said resulting solution in the form of a saturated aqueous solution.

9. The process as claimed in claim 1, wherein, prior to catalyzing the cyclization of said arylthiourea, said resulting solution contains 2 to 20% by weight of water, relative to the sum of arylthiourea and sulfuric acid.

10. The process as claimed in claim 9, wherein said resulting solution contains 2.5 to 15% by weight of water, relative to the sum of arylthiourea and sulfuric acid.

11. The process as claimed in claim 9, wherein said resulting solution contains 3 to 8% by weight of water, relative to the sum of arylthiourea and sulfuric acid.

12. The process as claimed in claim 9, wherein said sulfuric acid is 100% strength sulfuric acid and wherein said resulting solution contains 3 to 8% by weight of water, relative to the sum of arylthiourea and sulfuric acid.

13. The process as claimed in claims 1 or 2, wherein the product of said process is precipitated out as the sulfate salt of said compound of formula (I).

14. The process as claimed in claims 1 or 2, wherein, subsequent to said catalyzing step, which results in the formation of the sulfate salt of said 2-aminobenzothiazole of formula (I), this resulting sulfate salt is converted to the corresponding free base by addition of an alkali metal hydroxide solution or aqueous ammonia solution, followed by isolation of a said compound of formula (I).

15. The process as claimed in claim 1, wherein the product of said process is 4-chloro-, 6-chloro-, 5,6-dichloro-, 4-fluoro-, 6-fluoro-, 6-nitro-, 4-nitro-, 6-methoxy-, 6-ethoxy-, 6-methyl-, 6-ethyl-, 4-trifluoromethyl-, or 6-trifluoromethyl-2-aminobenzothiazole.

16. The process as claimed in claim 1, wherein the arylthiourea of the formula (II) is 2-chloro-, 4-chloro-, 3,4-dichloro-, 2-fluoro-, 4-fluoro-, 4-trifluoromethyl-, 2-nitro-, 4-nitro-, 4-methoxy-, 4-ethoxy-, 4-methyl-, 2-methyl, 2-ethyl-, or 4-ethylphenylthiourea.

17. The process as claimed in claim 1, wherein the conversion is carried out with a 2 to 3.4-fold amount by weight of sulfuric acid, relative to said arylthiourea.

18. The process as claimed in claim 1, wherein said catalyzing step is carried out with an amount of 0.01 to 10 mol % of bromine or bromide, relative to the amount of arylthiourea used.

19. The process as claimed in claim 1, wherein said dissolving and catalyzing steps are carried out at a temperature of 10° to 130° C.

* * * * *